United States Patent

Watanabe et al.

[11] Patent Number: 5,415,649
[45] Date of Patent: May 16, 1995

[54] DISPOSABLE DIAPERS

[75] Inventors: Hisanori Watanabe, Utsunomiya; Kenji Ando, Ichikai; Haruko Kawaguchi, Utsunomiya, all of Japan

[73] Assignee: KAO Corporation, Tokyo, Japan

[21] Appl. No.: 784,531

[22] Filed: Oct. 29, 1991

[30] Foreign Application Priority Data

Oct. 31, 1990 [JP] Japan .................................. 2-294896
Apr. 4, 1991 [JP] Japan .................................. 3-099623
Jun. 4, 1991 [JP] Japan .................................. 3-132966

[51] Int. Cl.$^6$ ............................................. A61F 13/15
[52] U.S. Cl. .................................................. 604/385.2
[58] Field of Search ................... 604/358, 385.1, 385.2, 604/394, 396

[56] References Cited

U.S. PATENT DOCUMENTS

| | | |
|---|---|---|
| 2,733,715 | 2/1956 | Folk . |
| 2,954,770 | 10/1960 | Roth . |
| 3,860,003 | 1/1975 | Buell . |
| 4,205,679 | 6/1980 | Repke et al. . |
| 4,323,070 | 4/1982 | Ternström et al. ............... 604/385.2 |
| 4,641,381 | 2/1987 | Heran et al. . |
| 4,646,362 | 3/1987 | Heran et al. ............... 604/385.2 X |
| 4,681,580 | 7/1987 | Reising et al. ................ 604/385.2 |
| 4,753,646 | 6/1988 | Enloe ............................. 604/385.2 |
| 4,938,754 | 7/1990 | Mesek ............................ 604/385.2 |
| 5,037,417 | 8/1991 | Ternström et al. ............... 604/385.2 |

FOREIGN PATENT DOCUMENTS

| | | |
|---|---|---|
| 0048011 | 3/1982 | European Pat. Off. . |
| 0172036 | 2/1986 | European Pat. Off. ............ 604/358 |
| 0187727 | 7/1986 | European Pat. Off. . |
| 0241925 | 10/1987 | European Pat. Off. . |
| 52-40267 | 10/1977 | Japan . |
| 61-207605 | 9/1986 | Japan . |
| 24364 | 1/1990 | Japan . |

Primary Examiner—Randall L. Green
Assistant Examiner—Mary Beth Jones
Attorney, Agent, or Firm—Birch, Stewart, Kolasch & Birch

[57] ABSTRACT

In a disposable diaper including a body having a liquid permeable topsheet, a liquid impermeable backsheet, and an absorbent member interposed therebetween, the body being divided into a stomach portion which, when in wear, is located on a wearer's stomach side and a back portion which, when in wear, is located on his back side, the stomach portion and the back portion being connected and fixed together at both side edge portions, respectively, of the stomach and back portions to form a pair of leg opening portions and a unitary waist opening portion, the waist opening portion and pair of leg opening portions being provided around entire peripheral edges thereof with elastic members forming substantially continuous gathers.

6 Claims, 5 Drawing Sheets

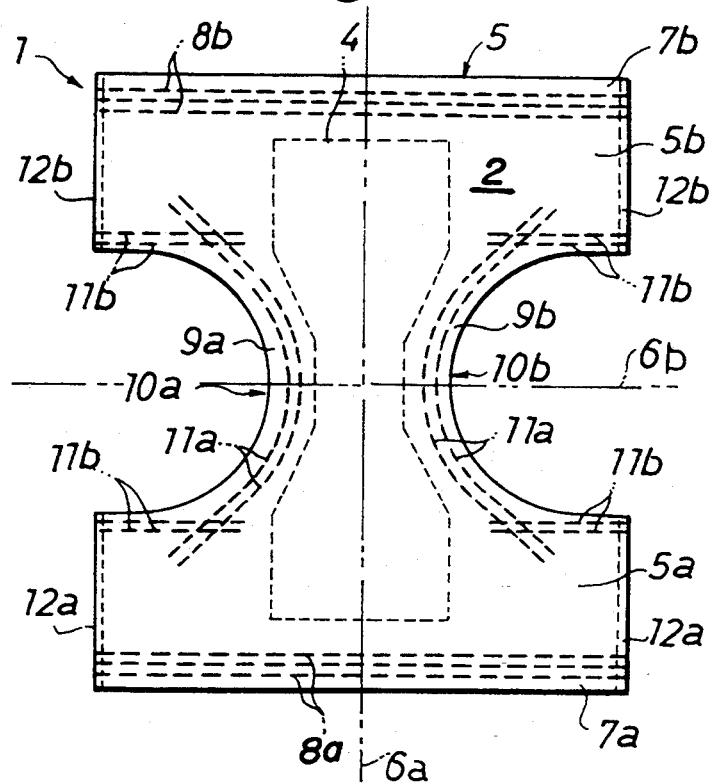
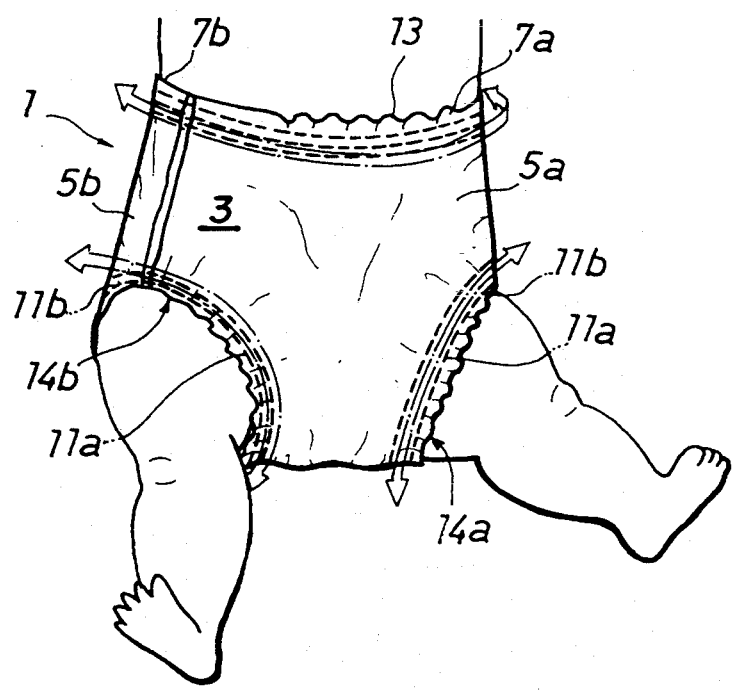

DISPOSABLE DIAPERS

BACKGROUND OF THE INVENTION

1. Field of the Invention

This invention relates to a disposable diaper for infants, adults or incontinent persons, and particularly to a shorts type disposable diaper.

2. Description of the Prior Art

In general, disposable diapers include a vertically long body comprising a liquid permeable topsheet, a liquid impermeable backsheet, and an absorbent member interposed therebetween, the body being divided into a stomach portion which, when in wear, is located on the stomach side of its user and a back portion which, when in wear, is located on his back side.

As a known disposable diaper of this type, there is, for example, a flat type in which both side edges (side flaps) of the back portion are provided with fastening devices which, when in use, are fastened to the stomach portion of the body (Japanese Patent Publication No. Sho 52-40267).

There have been there was proposed a shorts type disposable diaper in which a pair of right and left side flaps formed along both longitudinal sides of the diaper body are connected and fixed together at both stomach and back portions to form a pair of right and left leg opening portions and a unitary waist opening portion (Japanese Patent Early Laid-open Publication No. Sho 61-207605). In the shorts type disposable diaper, both the pair of leg opening portions and the unitary waist opening portion are designed to be expansible so as to fit to the wearer's body. Usually, since the wearer can wear this shorts type disposable diaper in an upright position, it is used as a toilet training underwear for a baby to enable him to be free from a diaper as soon as possible. It is also usable for an incontinent person, or an adult who can walk.

The shorts type disposable diaper of this type has such feature, when compared with the so-called flat type diaper, as that the wearer can pull it up and down by himself just like normal underwear. In order to satisfy the requirement that the wearer himself can easily wear the diaper without leakage of waste,materials, the shorts type disposable diaper is required to have an excellent fitness. Moreover, the diaper is required to have a favorable compliance to the wearer's busy action.

In order to meet with such requirements as mentioned above, Japanese Patent Early Laid-open Publication No. Hei 2-4364 discloses a constitution, wherein an expansible side panel (side member) is provided to side portions for connecting a stomach portion with a back portion of a body, and elastic members are provided to an end portion of the stomach side and an end portion of the back side of the body.

That is, as is shown in FIG. 8, in a body 55 of a conventional diaper 51, an under-crotch portion is provided at both side edges thereof with side flaps 59a, 59b extending outward of an absorbent member 54, and the body 55 is provided at both end portions thereof with waist flaps 57a, 57b extending outward of the absorbent member 54, the side flaps 59a, 59b of the under-crotch portion being provided with elastic members 61, 61 which are arranged thereon in expansible states. Similarly, the waist flaps 57a, 57b are provided with elastic members 58a, 58b which are arranged thereon in expansible states in order to enhance the fitness around the wearer's waist. The body 55 is provided on both sides of its back portion with side panels 62, 62 and on both sides of its stomach portion with side panels 63, 63. Each of the side panels 62 and 63 are formed of an elastic member which is a separate member from the body 55, and the side panels 62 and 63 are connectable with each other at end portions 64, 64 thereof.

However, owing to the correlation of expanding lines of stress (indicated by two-headed arrows with empty inside in FIG. 9 at the leg opening portions and at the waist opening portion, which respectively are formed by the elastic members 61, 58a, 58b and the side panels 62, 63 having elasticity, as shown in its worn state in FIG. 9, the conventional shorts type disposable diaper 51 has the following problems.

The expression "expanding lines of stress" refers to expansible portions applied with gatherings formed of an elastic member.

That is, although the expanding lines of stress of the respective opening portions intersect with each other when they are extended, a gap portion X is sometimes formed between adjacent expanding lines of stress, the gap portion X where no expanding line of stress exists. For example, when the wearer is in a bending attitude, gaps X are formed between the diaper and the wearer at his stomach portion, and these gaps X are to be a cause of leakage.

Further, it has such problems as that since the side panels 62, 63 are formed of a separate member from the body, the number of component parts of the diaper is increased and the manufacturing process becomes complicated, thus resulting in high cost.

Furthermore, the side panels 62, 63 are of a unitary member, and the physical property of each portion is the same. Accordingly, in order to increase the fastening force for preventing a slip-down and enhancing the fitness, the expansion of the whole side panels 62, 63 is required to be increased. However, if the expansion is increased, an excessive oppressive sensation is given to the wearer or the increased expansion jeopardizes the wearer's smooth pulling-on and pulling-off performance.

SUMMARY OF THE INVENTION

An object of the present invention is to provide a disposable diaper for preventing the leakage of waste material at a reduced cost.

The present invention has achieved the above object by providing a disposable diaper including a body having a liquid permeable topsheet, a liquid impermeable backsheet, and an absorbent member interposed therebetween, said body being divided into a stomach portion which, when in wear, is located on a wearer's stomach side and a back portion which, when in wear, is located on his back side, the stomach portion and the back portion being connected and fixed together at both side edge portions, respectively, of said stomach and back portions to form a pair of leg opening portions and a unitary waist opening portion, wherein the waist opening portion and pair of leg opening portions are provided around entire peripheral edges (which are also referred to as surrounding portions) thereof with elastic members forming substantially continuous gathers.

Furthermore, the present invention has achieved the above object by providing a disposable diaper including a body having a liquid permeable topsheet, a liquid impermeable backsheet, and an absorbent member interposed therebetween, connecting and fixing a stomach portion located on a wearer's stomach side and a back portion located on his back side together at both side edge portions, respectively, of the stomach and back portions to form a unitary waist opening portion, a pair of leg opening portions and a waist portion, and forming gathers around surrounding portions of the waist opening portion and the leg opening portions and at least part in the surrounding direction of the waist portion, wherein expanding stresses in the surrounding direction of the surrounding portions of the waist opening portion, the leg opening portions and the waist portion are different.

When the disposable diaper of the present invention is in wear, the substantially continuous gathers, which are integrally formed with the body, continuously act on both the waist opening and the pair of leg opening portions. As a result, no gap is formed between the diaper and its wearer and leakage of waste material from the diaper will be prevented.

The term "continuously" refers to a state where expanding lines of stress are continuous without interruption. It suffices, if, for example, the gathers are substantially continuous through the connected portion and they are not necessarily continuous elastic members.

Further, since the continuous gathers are integrally formed with the body of the diaper, the component parts can be reduced when compared with the prior art where the body is formed of a separate member, the manufacturing process can be simplified, and the manufacturing cost can be reduced.

Furthermore, the gathers of the present invention can be improved in fitness and handling by arranging a plurality of elastic members in juxtaposed relation or superposed relation.

BRIEF DESCRIPTION OF THE DRAWINGS

FIG. 1 is a view showing a developed state of a disposable diaper according to one embodiment of the present invention;

FIG. 2 is a perspective view of the disposable diaper of FIG. 1, showing a state when it is put on a wearer;

DETAILED DESCRIPTION OF THE EMBODIMENT

Figure 3:
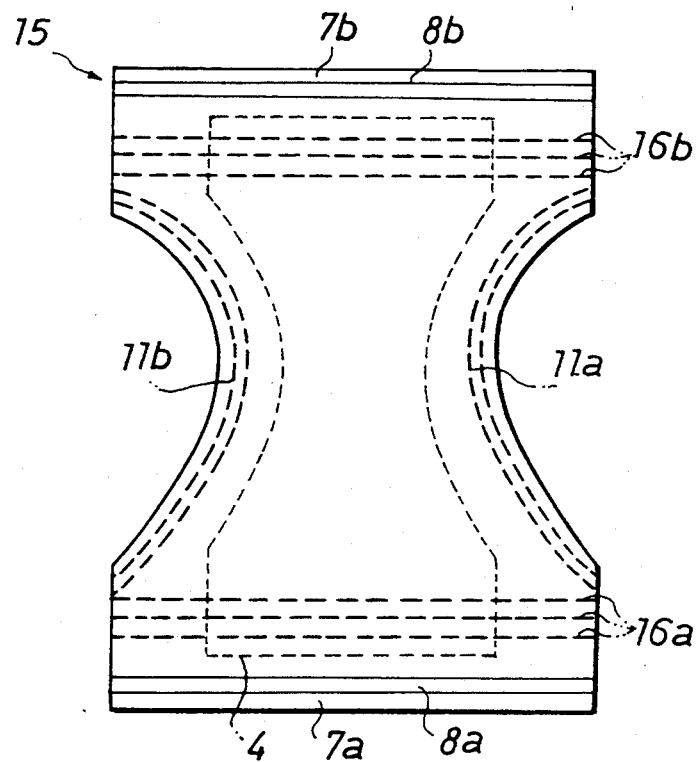
FIG. 3 is a view showing a developed state of a disposable diaper according to another embodiment of the present invention.

Several embodiments of the present invention will be described in detail with reference to FIGS. 1 through 5 of the accompanying drawings.

A disposable diaper 1 of the present invention includes a body which comprises a liquid permeable topsheet 2, a liquid impermeable backsheet 3 corresponding to the topsheet 2, and an absorbent member 4 fixedly interposed between both the topsheet 2 and backsheet 3 and adapted to absorb waste material.

The body 5 is divided into a stomach portion 5a which, when in wear, is located on the wearer's stomach side and a back portion 5b which, when in wear, is located on his back side, the stomach portion 5a and back portion 5b being symmetric with reference to a vertical center line 6a which is located generally at its center.

In the stomach portion 5a and back portion 5b of the body 5, the absorbent member 4 is provided on both longitudinal edges thereof with a pair of waist flaps 7a, 7b extending outward therefrom, elastic members 8a, 8b for forming a gather on each waist flap 7a, 7b, a pair of right and left side flaps 9a, 9b extending outward from both side edges of the absorbent member 4 in the width direction thereof, and elastic members 11a, 11b for forming a gather on each leg portion 10a, 10b of each side flap 9a, 9b, the side flaps 5b, 5a on both the back and stomach sides being partially connected and affixed at both the side edges 12b, 12a to form the waist opening portion 13 and a pair of right and left leg opening portions 14a, 14b (see FIG. 2).

The waist flaps 7a, 7b and the side flaps 9a, 9b are the overlapped portions of the topsheet and backsheet 2 and 3 and are integral with the body 5.

The elastic members 8a, 8b of the waist flaps 7a, 7b are continuously connected with the topsheet 2 and backsheet 3 as a plurality of yarn-like members arranged in generally parallel relation along the edges of the waist flaps 7a, 7b. When the waist opening portion 13 is formed by this, the elastic members 8a, 8b of the waist flaps 7a, 7b are continuously arranged along the peripheral edge of the waist opening portion 13. On the other hand, the elastic member 11a is accurate and the member 11b is linear. The arcuate elastic member 11a is formed in an arcuate configuration along a horseshoe shape of each leg portion 10a, 10b at the side flaps 9a, 9b. Further, the linear elastic member 11b linearly extends to a concave portion of the horseshoe shape in each side flap from each side flap 9a, 9b and intersected with the arcuate elastic member 11a. The elastic members 11a, 11b of this side flap are arranged adjacent to the edges of the pair of leg portions, that is, adjacent to the side edges of the side flaps 9a, 9b in the under-crotch area. The distance from the side edges to the outermost edges of the elastic members 11a, 11b of the side flap is preferably 0~50 mm and more preferably 0~20 mm and the distance from the outer edge of the absorbent member to the innermost edges of the elastic members 11a, 11b is preferably0~50 mm and more preferably 0~20 mm.

The elastic members 11a, 11b of the side flap are connected to the body 5 of the shorts type disposable diaper 1 in generally stretched states by known means, such as ultrasonic welding, heat welding, an adhesive agent, etc. Any material known in the art, such as yarn rubber, flat rubber, film type rubber or tape-like foam polyurethane can be used, and a unitary piece or a plurality of pieces may be used. In general, however, the elastic members 11a, 11b of the right and left side flaps are arranged in symmetric relation. The stress is preferably 70~100 g when they are stretched 150%. In order to prevent a gap at the opening portion, the stress of the elastic member 11a, 11b may be arranged to be different from each other. Alternatively the stresses of the outer elastic members of the respective members 11a, 11b may become higher than the inner elastic members.

The elastic members 8a, 8b of the waist flap are preferably of non-woven fabric type having expansibility, the expansibility being preferably larger in the width direction than in the longitudinal direction. The elastic members 8a, 8b of the waist flap are connected and fixed to the waist flaps 7a, 7b by known means in the art such as a hot melt adhesive agent, ultrasonic welding, heat welding, etc. Further, the elastic members 8a, 8b of this waist flap are connected in such states as being expansible.

The term "connected" used herein refers to a state where both the elastic members are contacted with each other in such a manner as to be able to generate at least an expanding line of stress as in the above term "continuously", and preferably connected in such a manner as to be, either directly or indirectly, superposed one upon the other.

The topsheet 2 is a liquid permeable sheet for enabling waste material to permente to the absorbent member 4 and preferably has a feel something like an undergarment. Examples of such liquid permeable sheet are preferably woven fabrics, nonwoven fabrics, perforated films and the like. The permeation leakage of waste materials such as urine and the like from the edge portion of the topsheet 2 can be prevented by applying a water repellent treatment to the peripheral edge portion of the top sheet by a method for applying a hydrophobic compound such as silicon series oil solution, paraffin wax and the like to the peripheral edge portion of the topsheet 2 or by a method for applying a hydrophilic compound such as alkyl phosphoric ester to the peripheral edge portion of the topsheet 2 in advance and then cleaning the peripheral edge with hot water.

The backsheet 3 is preferably a moisture permeable and liquid impermeable sheet able to permeate vapor therethrough and formed of a thermoplastic resin and filler added thereto and stretched and more preferably a sheet having a feel something like an undergarment. Examples of such liquid impermeable sheet are a composite material of film and a woven fabric or a composite material of film and a woven fabric.

The absorbent member 4 used in the disposable diaper 1 of this embodiment is preferably comprised of a fluff pulp as a chief component material and a high molecular water absorbent polymer as a secondary material, or a mixture of a thermoplastic resin, a cellulosic fiber and a high molecular water absorbent polymer subjected to heat treatment. The existing position of the high molecular water absorbent polymer may be in an upper layer, an intermediate layer or a lower layer, and the high molecular water absorbent polymer may be mixed with pulp. The high molecular water absorbent polymer preferably has an ability for absorbing and holding liquid more than twenty times the dead weight thereof and is in a grain shape having a property able to be gelled. Examples of such high molecular water absorbent-polymer are preferably starch-acrylic (salt) graft copolymer, a saponified material of starch-acrylonitrile copolymer, bridged material of sodium carboxymethylcellulose, acrylic (salt) polymer and the like.

The shorts type disposable diaper 1 of this embodiment can be obtained by folding the body of the diaper 1 back into a half along the horizontal center line 6b and connecting and fixing both side edges 12a, 12a of the back portion 5b to both side edges 12b, 12b of the stomach portion 5a. At this time, the elastic member 11b of the side flap located on the stomach portion 5a is superposed on the elastic member 11b of the side flap located on the stomach portion 5a, while the elastic member 8b of the waist flap 7b on the back side is superposed on the elastic member 8a of the waist flap 7a on the stomach side.

When the shorts type disposable diaper of this embodiment is in wear, as is shown in FIG. 2, a continuous gathering is formed at the pair of opening portions 14a, 14b by the elastic members 11a, 11b of the side flap, and a continuous gathering is formed at the waist opening portion 13 by the elastic members 8a, 8b of the back and waist flaps.

Accordingly, in the shorts type disposable diaper of this embodiment, the gather integrally and continuously formed on the body continuously acts on the waist opening portion 13 and the leg opening portions 14a, 14b to enhance the fitness to the wearer and also to surely prevent the leakage of waste material from the diaper.

Further, since the elastic members 8a, 8b of the waist flap and the elastic members 11a, 11b of the side flap are simply contacted with the body 5, the component parts can be reduced and the manufacturing process can be simplified.

Furthermore, by juxtaposing a plurality of elastic members 8a, 8a and 11a, 11b or intersecting them with each other, an ,expanding stress fitted to the wearer's body shape can be exhibited, thus enhancing fitness and preventing leakage.

Next, other embodiments of the present invention will be described with reference to FIGS. 3, 4 and 5.

Figure 4:
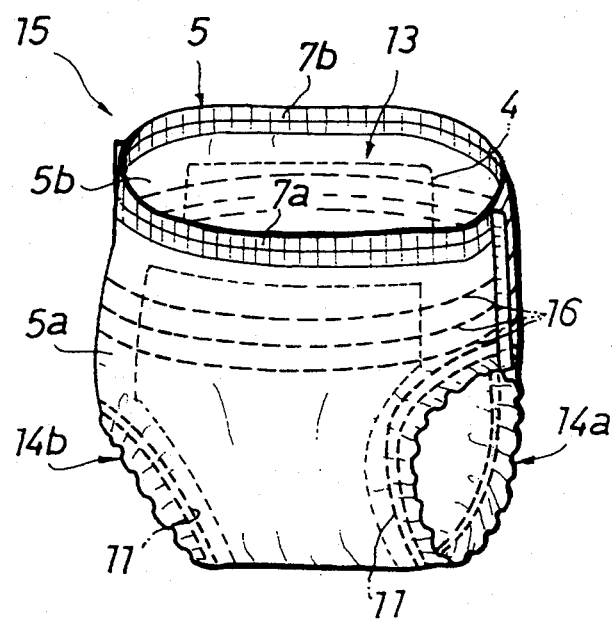
FIG. 4 is a perspective view of the disposable diaper of FIG. 3 in a wearable state.

In a disposable diaper 15 according to another embodiment shown in FIGS. 3 and 4, in addition to the elastic members 8a, 8b of the waist flap, a plurality of body-surrounding elastic members 16a, 16b are arranged continuously in a belt shape in the surrounding portion of a waist portion located between the waist opening portion and the leg opening portions (the area where the absorbent member 4 is disposed.)

Figure 5:
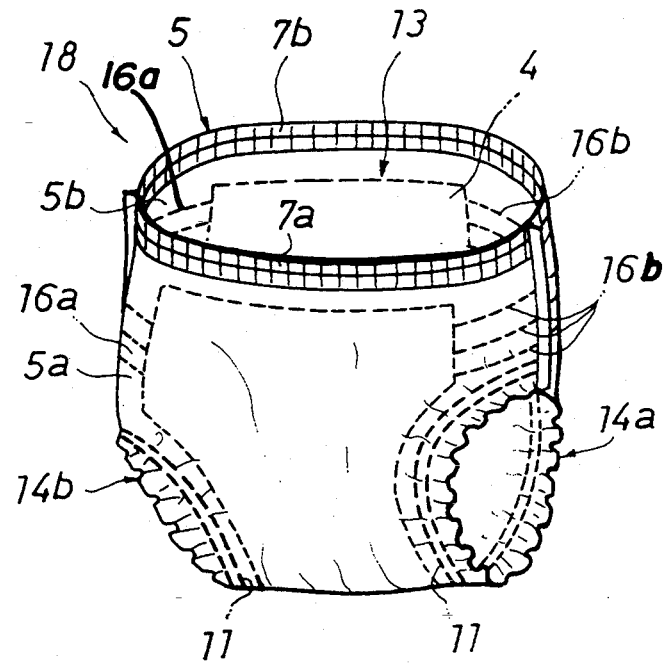
FIG. 5 is a perspective view of a disposable diaper according to still another embodiment of the present invention in a wearable state.

A disposable diaper 18 shown in FIG. 5 is different from the disposable diaper shown in FIGS. 3 and 4 in that body-surrounding elastic members 16a, 16b are arranged only at both side portions of the waist portion and not at the area where the absorbent member 4 of the embodiment shown in FIGS. 3 and 4 is disposed.

The elastic members 8a, 8b of the waist flap, the elastic members 11a, 11b of the side flap, and the body-surrounding elastic members 16a, 16b are preferably formed of natural rubbers, polyurethane, foam polyurethane, etc. and may be of yarn or belt form.

Since the disposable diaper 18 of this embodiment has the above-mentioned constitution, it does not slip out of place downward irrespective of any movements of the baby (wearer). In addition, since no gap is generated at the wearer's side, leakage of waste material can be prevented.

Still another embodiment of the present invention will be described with reference to FIGS. 6 and 7.

Figure 6:
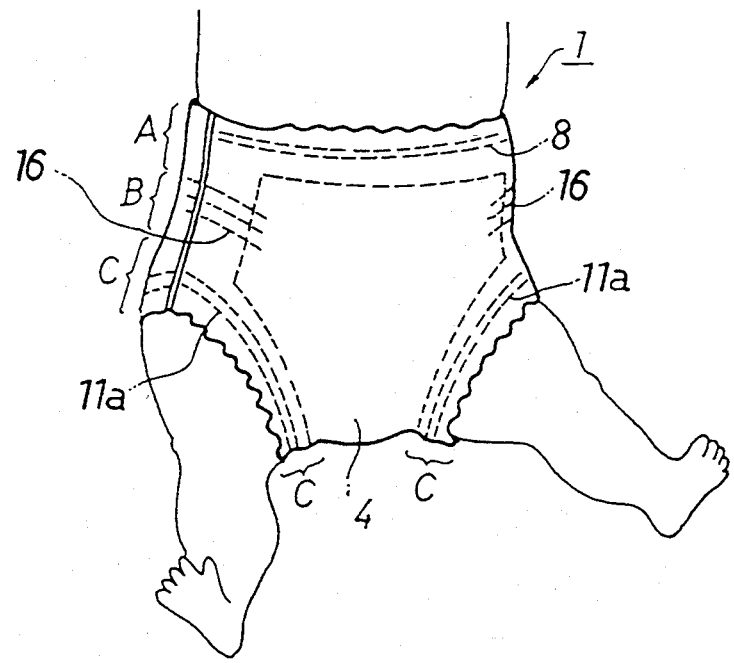
FIG. 6 is a perspective view of a disposable diaper according to still another embodiment of the present invention, in a wearable state.

The embodiment shown in FIG. 6 is constituted substantially the same as the embodiment shown in FIGS. 3 and 4 except for the following differences.

In the embodiment shown in FIG. 6, body-surrounding elastic members 16 are arranged at both side portions of the waist portion and at a part of the area where the absorbent member 4 is disposed.

In this embodiment, an elastic member 8 of a surrounding portion A of the waist opening portion is arranged around the surrounding portion A of the waist opening portion thereby forming a waist gather. The elastic members 11a, 11a of a surrounding portion C of the leg opening portions are arranged around the surrounding portion C of the leg opening portions thereby forming a leg gather.

The elastic members 16, 16 of a surrounding portion B of the waist portion are arranged at both side portions of the waist portion and at a part of the area where the absorbent member 4 is disposed, as shown in FIG. 6, and a gather is formed in the surrounding portion B on which the elastic members 16, 16 are disposed, so that the surrounding portion B can fit the wearer's waist.

Referring to the elastic member 8 of the surrounding portion A, the elastic members 11a, 11a of the surrounding portion C and the elastic members 16, 16 of the surrounding portion B, it is preferable that those elastic members show the expanding stresses (per 5 mm in width and 10 mm in length in the expanding direction) of 10 to 120 g, 20 to 150 g and 30 to 300 g, in a 20% stretched state, in a 50% stretched state and in a 100% stretched state, respectively. The elastic members showing about 60 g, 140 g and 220 g, in a 20%, 50% and 100% stretched states, respectively, are used is this embodiment.

Figure 7:
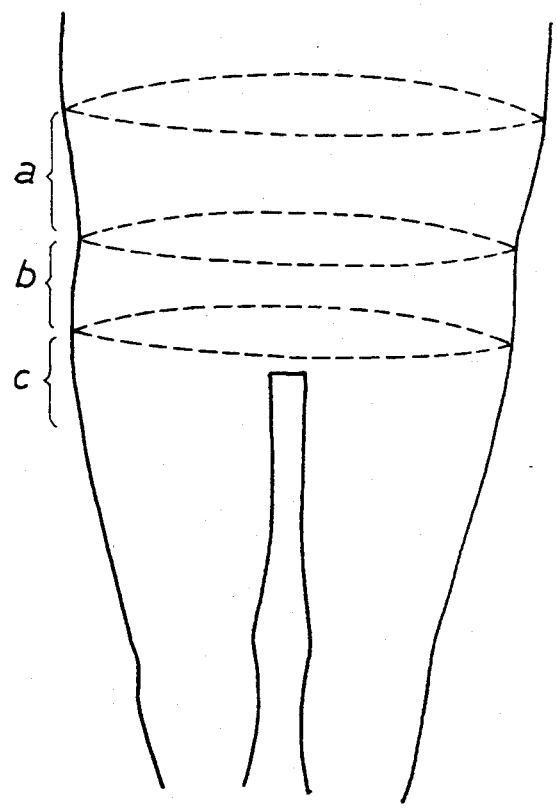
FIG. 7 is a explanatory view showing wearer's portions corresponding to the disposal diaper when the diaper of FIG. 6 is intended for wear.
Figure 8:
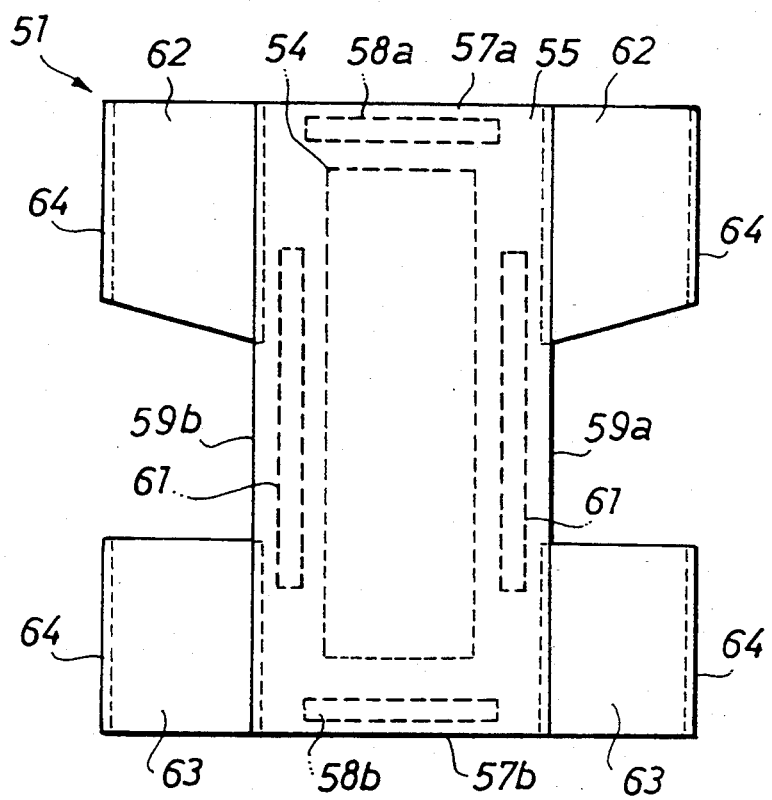
FIG. 8 is a view showing a developed state of the conventional disposable diaper.
Figure 9:
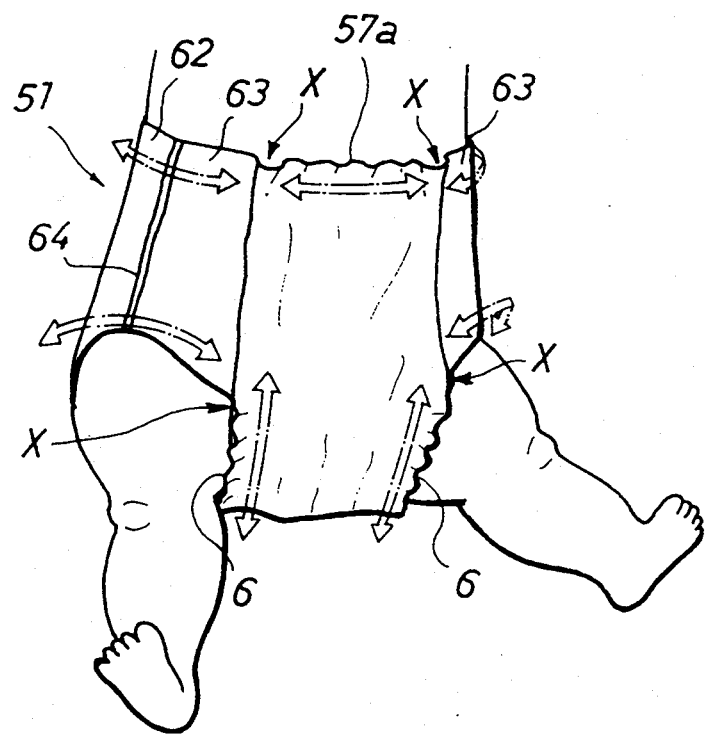
FIG. 9 is a perspective view of the conventional disposable diaper, showing a state when it is put on a wearer.

Furthermore, the surrounding portion A of the waist opening portion, the surrounding portion B of the waist portion and the surrounding portion C of the leg opening portions are, as shown in FIG. 7, disposed corresponding to a waist area a, a hipbone area b and a groin area c of a baby (wearer).

Since the surrounding length of the surrounding portion C of the leg opening portions pass over the groin of a wearer, it is largely affected by his activities and posture. Generally a baby has a figure that the hipbone area b is narrower than the waist area a and the groin area c to form a shape like a constricted barrel (like a sand glass shape). Therefore, the ordinary surrounding length of a diaper when it is worn is shown as surrounding portion A of the waist opening portion > the surrounding portion C of the leg opening portions > surrounding portion B of the waist portion. The maximum variation value (ΔA, ΔB, ΔC) due to wearer's postures and activities is shown as ΔA>ΔC>ΔB. The stress put on the each portion of the diaper is in relation to the surrounding portion A of the waist opening portion > surrounding portion C of the leg opening portions > surrounding portion B of the waist portion.

The surrounding length of the portions A, B and C of the diaper of the present invention varies. If the maximum value of the stresses (per 5 mm in width and 10 mm in length) in a 20% stretched state of the surrounding portions of said waist opening portion, said waist portion and said leg opening portions is 10 to 120 g, preferably 10 to 60 g, the maximum value of the stresses (per 5 mm in width and 10 mm in length) in a 50% stretched state thereof is 20 to 150 g, preferably 20 to 100 g and the maximum value of the stresses (per 5 mm in width and 10 mm in length) in a 100% stretched state thereof is 30 to 200 g, preferably 30 to 150 g, a wearer does not feel an oppressive sensation, and he can pull it on easily. Furthermore, no gap is generated in the surrounding portion A of the waist opening portion and in the surrounding portion C of the leg opening portion, so that an excellent effect to prevent slipping out of place downward and to prevent leaking can be obtained.

The above-mentioned explanation with reference to FIGS. 6 and 7 is also applied to the embodiments shown in FIGS. 3, 4 and 5.

(TEST EXAMPLE)

The following leak and slip tests were made using disposable diapers (diapers according to other embodiments) listed below.

TEST EXAMPLE 1

In this test, the disposable diaper shown in FIGS. 3 and 4 was prepared using the under-mentioned material and arranging four waist-surrounding elastic members 16a, 16b, which were in 180% expanded states, in the topsheet and backsheet.

Then, the following test was made using this disposable diaper 15. The results are shown in the Table listed below.

TOPSHEET 2
    Non-woven fabric formed of polypropylene (35 g/cm$^2$)

BACKSHEET 3
    Polyethylene film (thickness: 40μ)

ABSORBENT 4
    Composite material of fluff pulp and high absorbent polymer (bridged material of polyacrylic Na)

Elastic members 8a, 8b of waist flap
    Waist flap film width: 10 mm

Elastic members 11a, 11b of side flap
    Elastic rubber of 2 mm width: 4 pcs.

Waist-surrounding elastic member 16
    Urethane yarn rubber

<LEAK TEST AND SLIP TEST>

In this test, the above-mentioned disposable diaper 15 was put on a baby model of a weight of 10 Kg. After the baby model changed its attitude between a standing state and a sitting state 20 times, the slipping amount of the diaper was measured. Then, the model was laid horizontally or facing downward, an artificial urine (physiological saline solution) was supplied from a tube attached to the model so that the discharging speed of urine from its urine discharging portion will be 5 g/sec. The artificial urine was supplied until a leak occured, and the effect of the leak was observed. Further, an artificial soft feces mentioned below was supplied from the tube so that the feces discharging speed from its discharging portion will be 4 g/sec. The effect of prevention of feces leak was likewise observed in the model's horizontal lying state.

ARTIFICIAL SOFT FECES: Suspension of bentonite of 3 wt.% was adjusted to have a viscosity of 10 c.p. by carboxyethyl cellulose

TEST EXAMPLE 2

The disposable diaper 18 shown in FIG. 5 was prepared by providing four pieces of elastic material, which was in a 180% stretched state, between a topsheet and a backsheet around a part of a wearer's waist. Then, the above-mentioned test was made using this disposable diaper. The results are shown in Table listed below.

COMPARATIVE TEST EXAMPLE 1

In this test, a comparative item, in which the waist-surrounding elastic members 16a, 17a are not used, was prepared, and the same test as the test examples 1 and 2 was made. The results are shown in the Table listed below.

<EVALUATION OF TEST>

According to the results of the rests shown in the following Table 1, the diapers of the present invention were small in slipping length, large in absorbing amount of artificial urine and artificial feces and excellent in antileak compared with the comparative item.

TABLE

|  | Slipping length (mm) | Absorption until urine leak in horizontal state (g) | Absorption until urine leak in face-down state (g) | Absorption until feces leak in horizontal state (g) |
|---|---|---|---|---|
| Test 1 | 5 | 200 | 280 | 100 |
| item 2 | 10 | 180 | 250 | 90 |
| Comparative item | 40 | 70 | 120 | 40 |

That is, the disposable diaper 15 according to another embodiment of the present invention exhibits such effects as that the waist-surrounding part of the diaper 15 fits to the baby's body and leakage of waste material from a gap of the gather can be prevented, in addition to the above-mentioned effects.

It should be understood that the present invention is not limited to the above-mentioned embodiment and can be changed and modified within the spirit and scope of the present invention.

For example, the elastic members of the side flap are not limited to such constitution as that the elastic member 11a arranged in arcuate shape and the expansible member 11b arranged in linear shape intersect with each other. Alternatively, they may be arranged in a curved shape.

Furthermore, the elastic member 11b of the side flap is not limited to its linear arrangement but it may be arranged in a curved shape.

What is claimed is:

1. A disposable diaper including a body having a liquid permeable topsheet, a liquid impermeable backsheet, and an absorbent member interposed between the topsheet and backsheet, a stomach portion located on a wearer's stomach side and a back portion located on his back side and fixed together at both side edge portions, respectively, of said stomach and back portions to form a unitary waist opening portion, a pair of leg opening portions and a waist portion positioned between the waist opening portion and the pair of leg opening portions, and gathers formed circumferentially around each of said waist opening portion, said pair of leg opening portions and said waist portion, wherein;

expanding stresses in a 50% stretched state of the gathers of said waist opening portion, said leg opening portions, and said waist portion are such that the stress of the gathers of said waist opening portion is greater than the stress of the gathers of said leg opening portions which is greater than the stress of the gathers of said waist portion.

2. The disposable diaper according to claim 1, wherein the maximum value of the stresses(per 5 mm in width and 10 mm in length) in a 20% stretched state of the gathers of said waist opening portion, said waist portion and said leg opening portions is 10 to 120 g, the maximum value of the stresses (per 5 mm in width and 10 mm in length) in a 50% stretched state thereof is 20 to 150 g, and the maximum value of the stresses (per 5 mm in width and 10 mm in length) in a 100% stretched state thereof is 30 to 200 g.

3. Disposable diaper as in claim 2, wherein the stresses in a 50% stretched state of said stomach portion and said back portion in the surrounding portion of said waist opening portion are different.

4. A pull-on disposable diaper comprising:
a liquid permeable topsheet;
a liquid impermeable backsheet;
an absorbent member interposed between said topsheet and said backsheet;
a unitary elasticized waist opening;
a pair of elasticized leg openings; and
means, positioned between said waist opening and said pair of leg openings and only on opposing side portions of said diaper, for conforming said diaper to natural body contours of a wearer,
wherein stresses in a 50% stretched state of said waist opening portion, said leg opening portions and said waist portion are such that the stress of said waist opening portion is greater than the stress of said leg opening portions which is greater than the stress of said waist portion.

5. The pull-on disposable diaper according to claim 1, wherein the maximum value of the stresses (per 5 mm in width and 10 mm in length) in a 20% stretched state of said waist opening portion, said waist portion and said leg opening portions is 10 to 120 g, the maximum value of the stresses (per 5 mm in width and 10 mm in length) in a 50% stretched state thereof is 20 to 150 g, and the maximum value of the stresses (per 5 mm in width and 10 mm in length) in a 100% stretched state is 30 to 200 g.

6. A pull-on disposable diaper comprising:
a liquid permeable topsheet;
a liquid impermeable backsheet;
an absorbent member interposed between said topsheet and said backsheet;
a unitary elasticized waist opening;
a pair of elasticized leg openings; and
means, positioned between said waist opening and said pair of leg openings and only on opposing side portions of said diaper, for conforming said diaper to natural body contours of a wearer,
wherein the maximum value of the stresses (per 5 mm in width and 10 mm in length) in a 20% stretched state of said waist opening portion, said waist portion and said leg opening portions is 10 to 120 g, the maximum value of the stresses (per 5 mm in width and 10 mm in length) in a 50% stretched state thereof is 20 to 150 g, and the maximum value of the stresses (per 5 mm in width and 10 mm in length) in a 100% stretched state is 30 to 200 g.

* * * * *